United States Patent [19]

Kaufman et al.

[11] Patent Number: 4,800,168
[45] Date of Patent: Jan. 24, 1989

[54] TWO REAGENT SYSTEM FOR THE COLORIMETRIC DETERMINATION OF CHLORIDE IONS IN BODY FLUIDS

[75] Inventors: Richard Kaufman, Belleville; Alex Wesolowski, Florham Park, both of N.J.

[73] Assignee: Hoffmann-La Roche Inc., Nutley, N.J.

[21] Appl. No.: 788,280

[22] Filed: Oct. 17, 1985

[51] Int. Cl.$^4$ .......................................... G01N 33/483
[52] U.S. Cl. ................................... 436/124; 436/125; 436/175; 436/177
[58] Field of Search ................ 436/124, 125, 175, 177

[56] References Cited

U.S. PATENT DOCUMENTS

| | | | |
|---|---|---|---|
| 3,185,549 | 5/1965 | Hamilton | 436/125 |
| 3,964,864 | 6/1976 | Dahms | 436/68 X |
| 4,278,440 | 7/1981 | Law et al. | 436/125 |
| 4,393,142 | 7/1983 | Stephans | 422/61 X |

FOREIGN PATENT DOCUMENTS 2153387 5/1973 Fed. Rep. of Germany ...... 436/125

OTHER PUBLICATIONS

Kirk–Othmer, Encyclopedia of Chemical Technology, 3rd Ed., vol. 5, pp. 339, 351–355.
Luce, E. M. et al., Industrial and Engineering Chemistry, vol. 15, pp. 365–366.
Liedtke, R. J. et al., Clin. Chem., vol. 27, No. 12, pp. 2025–2028, 1981.
Tietz, N. W., Ed., Fundamentals of Clinical Chemistry, pp. 624–625, 1970.
McKittrick, D. S. and C. L. A. Schmidt, Arch Biochem, 6:273, 1945.
Iwasaki, I. et al., Bull Chem Soc (Japan), 25:226, 1952.
Zall, D. M. et al., Analytical Chemistry, 28:1655–1668, 1956.

*Primary Examiner*—Barry S. Richman
*Assistant Examiner*—Jill Johnston
*Attorney, Agent, or Firm*—Jon S. Saxe; George M. Gould; Julie M. Prlina

[57] ABSTRACT

A method for measuring chloride ion concentration in a sample of body fluid, e.g., serum or plasma is described in which a sample blank is made in the same cuvette after the test measurement has been made.

16 Claims, No Drawings

TWO REAGENT SYSTEM FOR THE COLORIMETRIC DETERMINATION OF CHLORIDE IONS IN BODY FLUIDS

BACKGROUND OF THE INVENTION

Chloride ion is the major extra-cellular anion. Thus, it is significantly involved in maintaining proper hydration, osmotic pressure, and normal anion-cation balance in warm-blooded animals like humans. Clinically, chloride ion loss is associated with chronic pyelonephritis. Low serum chloride values may be observed in those types of metabolic acidosis (e.g., diabetic acidosis and renal failure) that are caused by excessive production or diminished secretion of acids. High serum chloride values are observed in dehydration and in conditions causing decreased renal blood flow, such as congestive heat failure. Accordingly, an accurate, economical and convenient method for determining chloride ion levels in body fluids is a very valuable tool for the clinical chemist.

A variety of methods have been used to measure chloride ions in body fluids such as serum. Among the most common of these methods are coulometric-amperometric titrations, end point titrations using mercuric nitrate and diphenylcarbazone, and colorimetric methods using mercuric thiocyanate-ferric nitrate. (Tietz, N. W. ed., Fundamentals of Clinical Chemistry, 2nd Ed., pp 879-884, 1976, WB Saunders Co., Philadelphia, PA).

Due to the complexity of many body fluids, e.g., serum, it is usually necessary with most of the prior art methods, except for the colorimetric-amperometric method, to remove protein from the sample before making chloride measurements. This is usually accomplished by making a protein-free filtrate using protein precipitating acids (e.g. tungstic acid) or through dialysis, where the dialyzing membrane retains large molecules, such as serum proteins, and allows only small ions such as chloride to pass through.

The drawback to the aforementioned procedures, however, is that removal of protein from the sample is not well suited for most clinical chemistry analyzers or manual assays. The precipitation methods require additional reagents, mixing, centrifugation or filtration, and decanting prior to the actual chloride measurement. With the dialysis procedures, specially designed equipment is necessary and procedures using this methodology have largely been limited to Auto Analyzer ® methods. In the case of serum chloride, measurements made without protein removal on a centrifugal or similar clinical analyzer as for example, a COBAS BIO ® Centrifugal Analyzer (Roche Diagnostic Systems, Division of Hoffmann-La Roche Inc., Nutley, N.J. 07110) using the mercuric thiocyanate-ferric nitrate method may result in errors being made if sample blanks are ignored.

Frequently, the sample of body fluid being assayed for chloride ion content will contain endogeneous compounds, e.g., lipids or chylomicrons (lipids bound to protein) that absorb or scatter light at the wavelength maximum of the ferric thiocyanate complex formed when chloride ion concentration is measured using the ferric nitrate-mercuric thiocyanate procedure. Thus, certain samples, especially lipemic sera, may cause over-recovery of the chloride ion concentration in the sample. This can be illustrated by Equation 1, where $A_1 + A_2 + \ldots A_n$ are compounds present in the sample that absorb at or near the wavelength of the ferric thiocyanate complex being measured.

EQUATION 1

$$A_1 + A_2 + \ldots A_n + 2Fe(NO_3)_3 + 3Hg(SCN)_2 + 6Cl^- \rightleftharpoons 2Fe(SCN)_3 + 3HgCl_2 + 6NO_3^- + A_1 + A_2 + \ldots A_n.$$

In the reaction illustrated by Equation 1, the chloride ions displace the thiocyanate ions from the mercuric ions. The displaced thiocyanate ions are then complexed by iron (III) to form the colored ferric thiocyanate complex which is proportional to the chloride ion concentration in the sample. As is readily apparent, if the sample contains compounds that absorb or scatter light at or near the absorbance wavelength of the $Fe(SCN)_3$ complex, some form of sample blanking is needed to correct for the interference.

It can thus be appreciated that some form of sample blanking is necessary when determining chloride ion concentration in body fluids like serum or plasma, if accurate measurements are to be obtained using the ferric nitrate-mercuric thiocyanate procedure. Classically, sample blanking is accomplished by running the samples in a solution similar to the chloride reagent but without the ferric nitrate. Although this procedure is effective, it requires additional sample and decreases the throughput of the assay by a factor of two since a separate run and an additional cuvette is needed for the sample blank.

A procedure wherein chloride ion measurement can be made without the removal of protein from the sample and without the need for additional sample and an additional cuvette for a sample blank is thus desirable. The present invention provides to a two reagent system for the determination of chloride ion wherein the sample blank measurement is made after the test measurement using the original cuvette and sample.

SUMMARY OF THE INVENTION

The invention relates to a method for measuring chloride ion concentration in a sample of body fluid, for example, serum, plasma or urine in which a sample blank is made in the same cuvette after the test measurement has been made. The invention comprises the steps of:

(1) Mixing a sample of body fluid with a water-soluble color reagent containing $Fe^{+++}$ $Hg^{++}$ and $SCN^-$ ions;

(2) Measuring the absorbance of the mixture of Step 1 at from about 450 to about 550 nm;

(3) Adding an iron complexing reagent to the mixture of Step 2 wherein said iron complexing reagent complexes iron and forms essentially colorless complexes with $Fe^{+++}$ and $Hg^{++}$; and (4) Measuring the absorbance of the mixture of Step 3 at from about 450 to about 550 nm.

The difference between the second absorbance measurement and the first absorbance measurement is proportional to the chloride ion concentration in the sample.

DETAILED DESCRIPTION OF THE INVENTION

The invention is directed to a colorimetric method for measuring chloride ion concentration in a sample of body fluid which method comprises the steps of:

(1) Mixing a sample of body fluid with a color reagent;
(2) Measuring the absorbance of the mixture of Step 1 at from about 450 to 550 nm;
(3) Adding an iron complexing reagent to the mixture of Step 1; and
(4) Measuring the absorbance of said mixture of Step 3 at from about 450 to about 550 nm;

wherein the difference between the second absorbance measurement and the first absorbance measurement is proportional to the chloride ion concentration in said sample.

The method of the invention provides a procedure whereby a sample blank measurement is made on the same sample and in the same cuvette after the test chloride measurement has been made. Using Equation 2 for the purposes of illustration, an absorbance measurement is made at about 450 to about 550 nm after the reaction has reached equilibrium. An iron complexing reagent containing e.g., disodium ethylene diamine-tetraacetic acid (EDTA) is added which chelates the ferric ions to form the essentially colorless Fe(EDTA) complex. The remaining absorbance of the solution will be due to the reagent absorbance and the sample absorbance. Thus, the net absorbance of the assay, due to the presence of chloride ion, will be the initial absorbance (before EDTA addition) less the absorbance after EDTA addition and corrections if necessary for volume dilution.

Equation 2

$$Fe(SCN)_3 + HgCl_2 + NO_3^- + A_1 + A_2 + \ldots A_n + EDTA \rightarrow Fe(EDTA) + 2Cl^- + NO_3^- A_1 + A_2 + \ldots A_n + 3SCN^- + 2Hg(EDTA).$$

As used herein, the term "body fluid" refers to human or animal serum, plasma, sweat, urine and the like. The method of the invention is particularly suited for determining chloride ion concentration in serum and plasma samples and especially, human serum and plasma samples.

As used herein, the term "color reagent" refers to an aqueous solution of $Fe^{+++}$, $Hg^{++}$ and $SCN^-$ ions. In general any compound which is soluble in water and which dissociates to release $Fe^{+++}$, $Hg^{++}$ and $SCN^-$ ions and which does not give unwanted side reactions with the sample or the iron complexing reagent can be used herein. Compounds which may be used to provide $Fe^{+++}$ ions are ferric nitrate, ferric sulfate, ferric malate, ferric lactate, and the like. Preferred for use herein is ferric nitrate. Illustrative compounds which can be used to provide a source of $Hg^{++}$ ions are mercuric nitrate, mercuric acetate and mercuric benzoate. Preferred for use herein is mercuric nitrate. Water-soluble salts of thiocyanate can be used to provide $SCN^-$ ions. Preferred for use herein is sodium thiocyanate.

A suitable color reagent for use herein contains from about 60 to about 80 millimoles (mmol) per liter of ferric nitrate, from about 1.75 to 2.75 mmol per liter of mercuric nitrate, and from about 2.75 to about 3.75 mmol per liter of sodium thiocyanate. Preferred for use herein is a color reagent containing from about 70 to about 80 mmol per liter ferric nitrate, from about 2.0 to about 2.5 mmol per liter of mercuric nitrate and from about 3.0 to about 3.5 mmol per liter of sodium thiocyanate, especially preferred for use herein is a color reagent containing 75 mmol per liter of ferric nitrate, 2.22 mmol per liter of mercuric nitrate and 3.3 mmol per liter of sodium thiocyanate.

The term "iron complexing reagent", as used herein, refers to an aqueous solution containing a water-soluble compound(s) capable of complexing $Fe^{+++}$ and which will form an essentially colorless complex with $Fe^{+++}$ and $Hg^{++}$ ions. Many such materials, for example salts of ethylenediamine tetraacetic acid (EDTA) and oxalate salts, are known and may be used herein. However, the salts of EDTA are preferred for use herein to prepare the iron complexing reagent. Especially preferred is the disodium salt of EDTA.

A preferred iron complexing reagent for use in the method of the invention contains from about 225 to about 325 mmol per liter of a salt of EDTA, and from about 275 to about 325 mmol per liter of a base, e.g., NaOH, KOH, etc. A particularly preferred ion complexing reagent for use herein comprises about 275 mmol per liter of disodium EDTA and about 300 mmol per liter of NaOH.

The absorbance of the sample can be measured using a conventional spectrophotometer. However, the colorimetric method for measuring chloride ion concentration of the invention is particularly suited for automated methods and more particularly suited for use with centrifugal analyzers. Illustrative of commercially available centrifugal analyzers are the COBAS BIO ® (Roche Diagnostic Systems), the CentrifiChem 400 (Union Carbide Corp.), and the Mullistat III centrifugal analyzer (Instrumentation Laboratory, Lexington, MA 08173). The method of the invention is preferably used with the COBAS BIO ® centrifugal analyzer.

The following example illustrates the method of the invention in greater detail. Said example is illustrative and is not intended to be limiting of the scope of the invention.

EXAMPLE 1

The chloride ion determination method of the invention is illustrated using the COBAS BIO ® Centrifugal Analyzer. The methodology and procedure for the assay are as follows:

Reagents:

|  | Concentration (mmol/L) |
|---|---|
| (1) Color Reagent | |
| Ferric Nitrate | 75 |
| Mercuric Nitrate | 2.2 |
| Sodium Thiocyanate | 3.3 |
| (2) Iron Complexing Reagent | |
| Disodium EDTA | 275 |
| Sodium Hydroxide | 300 |

The COBAS BIO ® was programmed using the following instrument parameters:

| PARAMETERS LISTING | |
|---|---|
| 1. UNITS | mmoL/L |
| 2. CALCULATION FACTOR | 0 |
| 3. STANDARD 1 CONC | 80 |
| 4. STANDARD 2 CONC | 100 |
| 5. STANDARD 3 CONC | 120 |
| 6. LIMIT | 120 |
| 7. TEMPERATURE (C.°) | 37.0 |
| 8. TYPE OF ANALYSIS | 6 |
| 9. WAVELENGTH (NM) | 510 |
| 10. SAMPLE VOLUME (UL) | 05 |

-continued

| PARAMETERS LISTING | |
|---|---|
| 11. DILUENT VOLUME (UL) | 25 |
| 12. REAGENT VOLUME (UL) | 150 |
| 13. INCUBATION TIME (SEC) | 120 |
| 14. START REAGENT VOLUME (UL) | 50 |
| 15. TIME OF FIRST READING (SEC) | .5 |
| 16. TIME INTERVAL (SEC) | 60 |
| 17. NUMBER OF READINGS | 02 |
| 18. BLANKING MODE | 1 |
| 19. PRINTOUT MODE | 1 |

The Color Reagent was added to the primary compartment of the COBAS BIO ® reagent tray and thereafter the Iron Complexing Reagent was added to the secondary reagent compartment. Chloride ion standards (80, 100, and 120 mmol/L) were added to the standard wells. After the samples and cuvette rotor had been added, the START button was pressed and assay was automatically made.

During the assay on the COBAS BIO ® the following events occured. The sample (5 μl) was mixed with 150 μl of the Color Reagent. After incubating for 120 seconds an absorbance measurement was made at 510 nm. The absorbance at this wavelength was primarily due to the $Fe(SCN)_3$ complex, the reagent, and sample background. Fifty (50) μls of the Iron Complexing Reagent was added and after a 60 second incubation a second absorbance reading at 510 nm was made. During the second incubation, the $Fe(SCN)_3$ complex was destroyed by the EDTA which formed the soluble and essentially colorless FeEDTA complex. The remaining absorbance of the solution was due to the sample background and reagent absorbance. Since the COBAS measures absorbances using a longitudinal light path, the difference between the absorbance readings will be due to $Fe(SCN)_3$ which is proportional to the chloride concentration in the sample.

EXAMPLE 2

A chloride ion recovery study was run in order to compare the precision of the ferric nitrate/mercuric thiocyanate method of determining chloride ion concentration using only a reagent blank as is conventional in the art, to the sample blanking procedure of the invention. Six (6) samples of human serum were assayed for chloride ion concentration using only a reagent blank, thereafter the samples were assayed for chloride ion concentration using the sample blanking method of the invention. ("Unspiked Sample"). Each sample was then "spiked" with a known amount (10 mMol/L) of chloride ion ("Spiked sample") and the concentration of chloride ion was again measured using only a reagent blank and using the sample blanking method of the invention. Percent Recovery is calculated as follows:

$$\left[\frac{A - B}{10}\right] \times 100 = \% \text{ Recovery}$$

A = Chloride Ion Concentration mmol/L In Spiked Sample
B = Chloride Ion Concentration mmol/L in Unspiked Sample.

The results are summarized in Table I.

TABLE I

| | % Recovery | |
|---|---|---|
| Sample No | Reagent Blank Only | Sample Blanking Method of the Invention |
| 1 | 68 | 96 |
| 2 | 77 | 99 |
| 3 | 115 | 102 |
| 4 | 104 | 96 |
| 5 | 87 | 114 |
| 6 | 69 | 99 |

What is claimed is:

1. A colorimetric method for measuring chloride ion concentration in a sample of body fluid which method comprises the steps of:
   a. Mixing a sample of body fluid with a water soluble color reagent comprised of about 60 to 80 mmol per liter $Fe^{+++}$, about 1.75 to 2.75 mmol per liter $Hg^{++}$, and about 2.75 to 3.75 mmol per liter $SCN^-$ ions;
   b. Measuring the absorbance of the mixture of Step a at from about 450 to 550 nm;
   c. Adding an iron complexing reagent comprised of about 225 to 325 mmol per liter of a salt of EDTA to the mixture of Step a; and
   d. Measuring the absorbance of said mixture of Step c at from about 450 to about 550 nm;
   e. Determining the chloride ion concentration from Steps b and d, wherein the difference between the second absorbance measurement and the first absorbance measurement is proportional to the chloride concentration in said sample.

2. A method according to claim 1 wherein said color reagent consists essentially of about 75 mmol per liter of ferric nitrate, from about 2.2 mmol per liter of mercuric nitrate and from about 3.3 mmol per liter of sodium thiocyanate.

3. A method according to claim 1 wherein said body fluid is selected from the group consisting of serum, plasma and urine.

4. A method according to claim 3 wherein said body fluid is selected from the group consisting of serum end plasma.

5. A method according to claim 1 wherein said color reagent consists essentially of from about 70 to about 80 mmol per liter of $Fe^{+++}$, from about 2.0 to about 2.5 mmol per liter of $Hg^{++}$ and from about 3.0 to about 3.5 mmol per liter of $SCN^-$.

6. A method according to claim 5 wherein said reagent consists essentially of about 75 mmol per liter of $Fe^{+++}$, about 2.22 mmol per liter of $Hg^{++}$ and about 3.3 mmol per liter of $SCN^-$.

7. A method according to claim 1 wherein said iron complexing reagent consists essentially of about 275 to about 325 mmol per liter of a salt of EDTA.

8. A method according to claim 7 wherein said iron complexing reagent consists essentially of about 275 mmol per liter of disodium EDTA and about 300 mmol per liter of an inorganic base.

9. A method according to claim 8 wherein the absorbance of said mixture of Step a and said mixture of Step c is measured at about 510 nm.

10. A method according to claim 9 wherein said absorbance is measured using a centrifugal analyzer.

11. A colorimetric method for measuring chloride ion concentration in a sample of body fluid which method comprises the steps of:

a. mixing a sample of body fluid with a water-soluble color reagent containing $Fe^{+++}$, $Hg^{++}$ and $SCN^-$ ions; wherein said water-soluble color reagent consists essentially of from about 60 to about 80 mmol per liter of $Fe^{+++}$, from about 1.75 to about 2.75 mmol per liter of $Hg^{++}$ and from about 2.75 to about 3.75 mmol per liter of $SCN-$;

b. measuring the absorbence of the mixture of Step a at from about 450 to 550 nm;

c. adding an iron complexing reagent to the mixture of Step a; wherein said iron complexing reagent consists essentially of about 225 to about 325 mmol per liter of a salt of EDTA; and d. measuring the absorbence of said mixture of Step c at from about 450 to about 550 nm;

e. determining the chloride ion concentration from steps b and d, wherein the difference between the second absorbence measurement and the first absorbence measurement is proportional to the chloride ion concentration in said sample.

12. A method according to claim 11 wherein said absorbence is measured using a centrifugal analyzer.

13. A method according to claim 11 wherein said body fluid is selected from the group consisting of serum or plasma.

14. A method according to claim 13 wherein said color reagent consists essentially of from about 70 to about 80 mmol per liter of $Fe^{+++}$, from about 2.0 to about 2.5 mmol per liter of $Hg^{++}$ and from about 3.0 to about 3.5 mmol per liter of $SCN^-$.

15. A method according to claim 14 wherein said reagent consists essentially of about 75 mmol per liter of $Fe^{+++}$, about 22.22 mmol per liter of $Hg^{++}$ and about 3.3 mmol per liter of $SCN^-$.

16. A method according to claim 15 wherein the absorbence of said mixture of Step a and mixture of Step c is measured at about 510 nm.

* * * * *